United States Patent
Kosmatopoulos et al.

(10) Patent No.: US 7,419,669 B2
(45) Date of Patent: Sep. 2, 2008

(54) PEPTIDE EPITOPES COMMON TO ANTIGENS OF THE SAME MULTIGENE FAMILY

(75) Inventors: Kostas Kosmatopoulos, Paris (FR); Stephanie Graff-Dubois, Paris (FR)

(73) Assignees: Institut Gustave Roussy, Villejuif (FR); Institut National de la Sante et de la Recherche Medicale, Paris (FR)

( * ) Notice: Subject to any disclaimer, the term of this patent is extended or adjusted under 35 U.S.C. 154(b) by 253 days.

(21) Appl. No.: 10/508,548

(22) PCT Filed: Mar. 27, 2003

(86) PCT No.: PCT/FR03/00970

§ 371 (c)(1), (2), (4) Date: Jun. 6, 2005

(87) PCT Pub. No.: WO03/083124

PCT Pub. Date: Oct. 9, 2003

(65) Prior Publication Data

US 2006/0263381 A1     Nov. 23, 2006

(30) Foreign Application Priority Data

Mar. 28, 2002  (FR) .................................. 02 03888

(51) Int. Cl.
*A61K 39/00* (2006.01)
(52) U.S. Cl. .................. 424/184.1; 424/185.1; 530/300
(58) Field of Classification Search ............ 424/184.1, 424/185.1; 530/300
See application file for complete search history.

(56) References Cited

FOREIGN PATENT DOCUMENTS

| WO | 00 20581 | 4/2000 |
|---|---|---|
| WO | 00 52045 | 9/2000 |
| WO | 01 41787 | 6/2001 |
| WO | 01 42267 | 6/2001 |

OTHER PUBLICATIONS

McIntyre et al, 1996, Cancer Immunol Immunother, 42: 246-250.*
Tanzarella, Silvia et al. "Identification of a Promiscuous T-Cell Epitope Encoded by Multiple Members of the MAGE Family", Cancer Research, vol. 59, No. 11, pp. 2668-2674, XP001132068, ISSN: 0008-5472 Jun. 1, 1999.
Graff-Dubois, Stephanie et al. "Generation of CTL Recognizing an HLA-A*0201-Restricted Epitope Shared by MAGE-A1,-A2,-A3,-A4,-A6,-A10, and -A12 Tumor Antigens: Implication in a Broad-Spectrum Tumor Immunotherapy", Journal of Immunology. vol. 169, pp. 575-580, XP001109368 Jul. 1, 2002.

* cited by examiner

*Primary Examiner*—Larry R. Helms
*Assistant Examiner*—Minh-Tam Davis
(74) *Attorney, Agent, or Firm*—Oblon, Spivak, McClelland, Maier & Neustadt, P.C.

(57) ABSTRACT

The invention relates to the production of peptide epitopes common to a plurality of antigens of the same multigene family, said epitopes containing at least one common pentapeptide sequence preceded by three amino acids at the N-terminal end and optionally followed by one or two amino acids at the C-terminal end. The invention also relates to polynucleotides coding for said epitopes. Said peptides and polynucleotides can be especially used in anti-tumour immunotherapy.

3 Claims, 6 Drawing Sheets

% of CD8 cells producing IFNγ

PEPTIDE EPITOPES COMMON TO ANTIGENS OF THE SAME MULTIGENE FAMILY

CROSS-REFERENCE TO RELATED APPLICATION

This application is a national stage of the international application PCT/FR03/00970, filed March 27, 2003, which claims benefit of the application FR 02/03888, filed Mar. 28, 2002.

The present invention relates to peptides representing shared epitopes of tumor antigens, and to their use in immunotherapy.

Peptide immunization or immunotherapy is a therapeutic approach which is currently the subject of great interest in the context of the prevention or treatment of cancers. The principle thereof is based on immunization with peptides which reproduce T epitopes of tumor antigens that are recognized by cytotoxic T lymphocytes (CTLs), which play a major role in the elimination of cancer cells expressing these antigens at their surface.

It will be recalled that CTLs do not recognize whole protein antigens, but peptide fragments thereof, presented by the major histocompatibility complex (MHC) molecules expressed at the surface of various cells. It is these peptide fragments which constitute the T epitopes. The peptides presented by the major histocompatibility complex class I (MHC I) generally have 8 to 11 amino acids, and are recognized by CD8+ T cells, which represent the major component of the cytotoxic response. The peptides presented by the major histocompatibility complex class II (MHC II) generally have 13 to 18 amino acids and are recognized by CD4+ T cells.

The identification of these epitopes, and in particular (given the essential role of the CD8+ response in cytotoxicity) of those presented by MHC I, therefore constitutes an essential step for the development of anti-tumor immunotherapy compositions.

Many tumor antigens are known at the current time; some of the T epitopes of these antigens have been identified and the effectiveness of vaccines based on peptides which reproduce these T epitopes has been shown in many cases.

However, the expression of the majority of tumor antigens is restricted to certain histological types of tumors, which limits their clinical use.

Another considerable limitation of peptide immunotherapy comes from the appearance, in certain patients, of tumor variants (escape variants) which no longer express the antigen recognized by the cytotoxic T lymphocytes.

Some tumor antigens belong to multigene families: within the same family there is a sequence homology, which may result in the existence of shared epitopes common to two or more members of the same family.

Generally, various members of the same family of antigens are expressed in various tumor types; the use of an epitope shared by these antigens could make it possible to obtain anti-tumor vaccines with a broad spectrum of activity.

Furthermore, in many cases, several antigens of the same family are co-expressed in the same tumor line; since the probability of loss of the expression of all these antigens is extremely low, the use of an epitope shared by these antigens may make it possible to avoid the appearance of escape variants.

Among the tumor antigens known to belong to a multigene family, mention will in particular be made of the antigens of the MAGE-A, HER, BAGE or GAGE families.

MAGE-A is a multigene family consisting of 12 homologous genes (MAGE-A1 to A12) located in the q28 region of the X chromosome (DE PLAEN et al., Immunogenetics. 40, 360, 1994). Among the members of this family, MAGE-A1, -A2, -A3, -A4, -A6, -A10 and -A12 are strongly expressed by tumors but not by normal tissues, with the exception of the testes and of the placenta.

The MAGE-A 1, 2, 3, 4, 6 and 12 antigens are present in a wide spectrum of tumors of very varied histological origin, such as melanomas, lung cancers, breast cancers, head and neck tumors, and sarcomas, myelomas, etc. (BRASSEUR et al., Int. J. Cancer, 52, 839, 1992; BRASSEUR et al., Int. J. Cancer, 63, 375, 1995; PELLAT-DECEUNYNCK et al., Eur. J. Immunol., 30, 803, 2000; OFUJI et al., Anticancer Res., 18, 3639, 1998; GIBBS et al., Melanoma Res., 10, 259, 2000; PATARD et al., Int. J. Cancer, 64, 60, 1995; OTTE et al., Cancer Res., 61, 6682, 2001; SUDO et al., J. Orthop. Res., 15, 128, 1997; LEE et al., Acta. Otolaryngol., 116, 633, 1996; HASEGAWA et al., Arch. Pathol. Lab. Med., 112, 551, 1998; YAMANAKA et al., Int. J. Mol. Med., 2, 57, 1998; GILLESPIE et al., Br. J. Cancer., 78, 816, 1998; TAHARA et al., Cancer, 85, 1234, 1999).

The expression of each MAGE-A antigen can vary from one tumor to another, but overall, the vast majority of tumors express at least one MAGE-A antigen.

The proteins of the HER family are also expressed by a large number of tumors of varied origin, such as breast tumor, ovarian tumor, bladder tumor, colon tumor, etc. (J. Cancer Res. Clin. Oncol. 2000, 126, 205; Clin. Cancer Res. 1999, 5, 4164; Clin. Cancer Res. 1999, 5, 3653; J. Cell Biochem. 1999, 73, 522; Br. J. Cancer 1994, 70, 459; Cancer Res. 2000, 60, 1483; Clin. Cancer Res. 2001, 7, 1957; Adv. Cancer Res. 1997, 71, 343; Stem cells, 1997, 15, 1; Science 1987, 235, 177; Cancer Res. 1990, 50, 4087).

Despite the potential advantage of using shared T epitopes, this approach has only been very rarely proposed. Mention will be made of the results of TANZARELLA et al. (Cancer Res., 59, 2668-74, 1999), who describe a peptide of sequence REPVTKAEML (SEQ ID No: 38) which constitutes an epitope common to several antigens of the MAGE-A family (MAGE-A 1, 2, 3 and 6) and which binds to the HLA-B*3701 allele of MHC-I.

The first obstacle to demonstrating other peptides constituting epitopes common to several tumor antigens of the same family is the rarity of the regions of appropriate size (at least 8 amino acids for a peptide presented by MHC I) that are completely identical from one antigen to another.

In order to overcome this obstacle, the inventors had the idea of investigating whether peptides exhibiting a lower percentage of identity could possess a common antigenic specificity, and found that an identity limited to the sequence of 5 amino acids extending from positions P4 to P8 of the peptide was sufficient.

The "sequence extending from positions P4 to P8" is defined here as the sequence beginning with the amino acid located at position 4 starting from the N-terminal end of the peptide, and ending with the amino acid located at position 8 starting from the N-terminal end of the peptide.

Consequently, a subject of the present invention is a method for identifying peptide epitopes presented by an HLA class I molecule and shared by at least two antigens of the same multigene family, characterized in that it comprises at least the following steps:

a) aligning the sequences of said antigens in order to identify on each of them a sequence of 8 to 10 amino acids having the following characteristics:

they comprise at least one common pentapeptide sequence preceded by 3 amino acids at the N-terminal end and, optionally, followed by one or two amino acids at the C-terminal end;

at least two of said sequences differ from one another by at least one amino acid positioned outside said pentapeptide sequence;

b) preparing the peptides corresponding to the sequences identified in step a).

According to a preferred embodiment of the method in accordance with the invention, it also comprises a step c) consisting in determining the binding affinity of each of the peptides prepared in step b) for the HLA class I molecule concerned, and the stability of the peptide/HLA class I molecule complex.

This step makes it possible to evaluate the potential immunogenicity of the peptides.

In fact, nonimmunogenic peptides most commonly exhibit a low affinity for the HLA class I molecule, and/or form with it a relatively unstable complex. Methods for determining the affinity of the peptide for the HLA molecule, and the stability of the complex formed, are known in themselves. Mention will be made, for example, of that described by FIRAT et al. (Eur. J. Immunol., 29, 3112, 1999).

The affinity of a peptide for an HLA molecule is most commonly defined relative to that of a reference peptide (for example IVGAETFYV (SEQ ID No: 1) for HLA-A*0201 or RPHERNGFTV (SEQ ID No: 2) for HLA-B*0702), in the form of relative affinity. The relative affinity is defined as the ratio of the concentration of the peptide tested to the concentration of the reference peptide allowing the formation, under the same conditions, of the same amount of peptide/HLA class I molecule complex. The higher the relative affinity, the lower the binding affinity of the peptide for the HLA class I molecule.

The stability of the peptide/HLA class I molecule complex is often defined by the $DC_{50}$, which represents the time required for the dissociation of 50% of the complexes formed.

Generally, the relative affinity is less than 5 and the $DC_{50}$ is greater than 2 hours in the case of potentially immunogenic peptides.

If the implementation of step c) reveals one or more potentially immunogenic peptides, the immunogenicity of said peptides can be verified, for example by conventional methods for determining the ability of this peptide to generate, in vivo, ex vivo or in vitro, a specific CTL response with respect to target cells loaded with this peptide, or expressing the antigen from which it is derived, or other antigens of the same family.

If no potentially immunogenic peptide is revealed in step c), the method in accordance with the invention comprises an additional step consisting in preparing a variant peptide, from the peptides obtained in step b), by substitution of one or more of the amino acids located outside the common pentapeptide sequence with one or more amino acids favorable to the immunogenicity, for example with one of the residues of the anchoring motif defined for the HLA class I molecule concerned. It is also possible to substitute the N-terminal amino acid with a tyrosine, as described in PCT application WO 02/08716.

The affinity of this variant peptide for the molecule concerned can be determined as indicated above. Its immunogenicity will then be verified by determining its ability to generate a specific CTL response with respect to the native peptide from which it is derived, and also with respect to the antigen from which this native peptide derives, and other antigens of the same family.

The implementation of the method in accordance with the invention has thus enabled the inventors to identify epitopes shared by the antigens of the MAGE-A family, and also epitopes shared by antigens of the HER family.

The inventors have in particular obtained, from a region common to the MAGE-A1, -2, -3, -4, -6, -10 and -12 antigens of the MAGE-A family, an immunogenic peptide presented by HLA-A*0201 and capable of inducing cytotoxic T lymphocytes which recognize all the MAGE-A antigens, and of lysing tumor cells expressing at least one antigen of the MAGE-A family.

This peptide, which is defined by the sequence (1-letter code): YLEYRQVPV (SEQ ID No: 3), is also part of the subject of the present invention.

Similarly, the inventors have obtained, from a region common to the HER1, 2, 3 and 4 antigens, an immunogenic peptide presented by HLA-A*0201 and capable of inducing cytotoxic T lymphocytes which recognize all the HER1, 2, 3 or 4 antigens and of lysing cells expressing at least one antigen of the HER family.

This peptide, which is defined by the sequence (1-letter code): YVWELMTFGV (SEQ ID No: 4), is also part of the subject of the present invention.

The peptide epitopes obtained in accordance with the invention, and in particular the peptides YLEYRQVPV (SEQ ID No: 3) and YVWELMTFGV (SEQ ID No: 4), can be used in the context of anti-tumor immunotherapy, for inducing a broad-spectrum CTL response, allowing the treatment of a large variety of tumors. In addition, in the case of peptides, such as the peptide YLEYRQVPV (SEQ ID No: 3), derived from the MAGE-A family, the expression of which outside the testes and the placenta, which are immunoprivileged tissues, is limited to only the tumor tissues, the risk of autoimmune reaction is considerably reduced.

A subject of the present invention is also compositions comprising at least one immunogenic peptide in accordance with the invention.

They may be multiepitope compositions capable of generating a polyspecific CTL response and which, with this aim, also comprise one or more other immunogenic epitope(s). These epitopes may be derived from the same antigen or from two or more different antigens.

These multiepitope compositions in accordance with the invention may also comprise at least one epitope presented by an MHC II molecule and capable of inducing a helper T response. They may also comprise, in order for it to be possible for them to be more widely used on a population in which the individuals carry different HLA alleles, one or more epitopes presented by MHC I molecules other than HLA-A*0201.

According to a preferred embodiment of a composition in accordance with the invention, it comprises at least one chimeric polypeptide comprising one or more copies of an immunogenic peptide in accordance with the invention. In the case of a multiepitope composition, said chimeric polypeptide also comprises one or more copies of at least one other immunogenic epitope.

Such a chimeric polypeptide can be readily obtained by methods known in themselves, and in particular by conventional recombinant DNA techniques.

A subject of the present invention is also the nucleic acid molecules encoding an immunogenic peptide or encoding a chimeric polypeptide in accordance with the invention.

A subject of the present invention is also the use of an immunogenic peptide epitope, of a composition or of a nucleic acid molecule in accordance with the invention, for obtaining a medicinal product, and in particular a medicinal product intended for anti-tumor immunotherapy.

The present invention also encompasses the medicinal products comprising, as active principle, at least one immunogenic peptide, one composition or one nucleic-acid molecule in accordance with the invention.

According to a preferred embodiment of the present invention, said medicinal products are vaccines.

Medicinal products in accordance with the invention may in addition comprise the usual excipients, and also adjuvants which are conventionally used in immunotherapy and which make it possible, for example, to promote the administration of the active principle, to stabilize it, to increase its immunogenicity, etc.

The present invention will be understood more fully from the further description which follows, which refers to non-limiting examples of implementation of the method in accordance with the invention for identifying shared epitopes in the MAGE-A family and in the HER family.

EXAMPLE 1

Figures 1A, 1B, 1C:
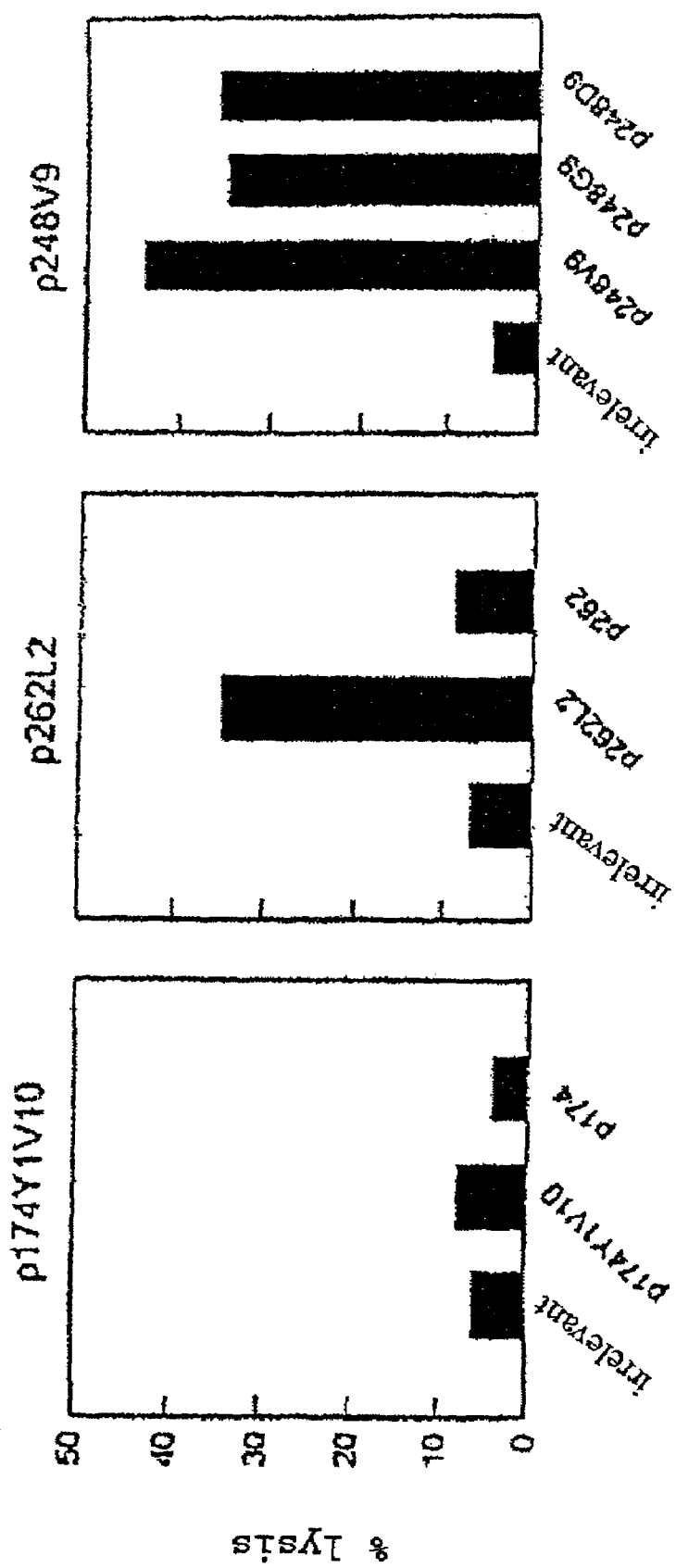
FIGS. 1A, B and C: Induction of specific cytotoxic T lymphocytes ("CTLs") by immunization with the variant MAGE-A peptides: (A) p174Y1V10(A) peptide; (B) p262L2 (B); and (C) p248V9(C). A cytotoxic effect for each peptide is compared to a control which is an irrelevant peptide.

Identification of Epitopes Presented by the HLA-A*0201 Molecule that are Shared by the MAGE-A 1, 2, 3, 4, 6, 10 and 12 Antigens I: Identification of Candidate Peptides:

In order to identify one or more epitopes shared by the various MAGE-A antigens and presented by the HLA-A*0201 molecule, the sequences of the MAGE-A antigens were aligned, and regions of 9 to 10 amino acids were selected on the basis of their homology between these antigens.

In the following description, these regions of 9 to 10 amino acids are denoted with reference to the position of their first amino acid in the MAGE-A1 sequence.

A single peptide, p262, was found identically in all the MAGE-A sequences. Another peptide, p174, was found identically in the MAGE-A1, -A2, -A3, -A4, -A6 and -A12 sequences.

In order to broaden the choice of the candidate peptides, a second search was carried out to select regions exhibiting complete sequence identity between positions P4 and P8. Two regions satisfied this criterion: 248 and 264. These sequences of the groups of peptides derived from these regions, and also that of the peptides p174 and p262, are represented in table I.

TABLE I

| Peptides | Sequences | MAGE-A antigen |
|---|---|---|
| 174 | CLGLSYDGLL (SEQ ID No: 5) | A1, A2, A3, A4, A6, A12 |
| 248 | YLEYRQVPG (SEQ ID No: 6) | A2, A3, A4, A6, A10, A12 |
|  | YLEYRQVPD (SEQ ID No: 7) | A1 |
| 262 | YEFLWGPRA (SEQ ID No: 8) | A1, A2, A3, A4, A6, A10, A12 |
| 264 | FLWGPRALV (SEQ ID No: 9) | A3, A12 |
|  | FLWGPRALI (SEQ ID No: 10) | A2, A6 |
|  | FLWGPRALA (SEQ ID No: 11) | A1, A4 |

The p248 group is made up of two peptides: p248G9 (MAGE-A2, -A3, -A4, -A6, -A10 and -A12) and p248D9 (MAGE-A1) which differ in terms of their C-terminal residue (position P9). The p264 group was excluded from the remainder of the study since it corresponds to an HLA-A*0201-restricted MAGE-A3 epitope (FLWGPRALV (SEQ ID No: 9)) that is already known, and it is also known that it is not efficiently processed by tumor cells (MICONNET et al., J. Biol. Chem., 275, 26892, 2000).

II: Affinity for HLA-A*0201 of the Selected Peptides, and Construction of Variants that are Potentially More Immunogenic The affinity of the selected peptides for HLA-A*0201 was defined by two parameters: the relative affinity (RA); which reflects the ability of the peptides to bind to HLA-A*0201, and the rate of dissociation of the HLA-A*0201/peptide complexes ($DC_{50}$), which reflects their stability. The peptides with high affinity (RA<5 and $DC_{50}$>2 hours) are potentially immunogenic, unlike the peptides with low affinity (RA>5 and $DC_{50}$<2 hours).

Relative Affinity:

Human T2 cells (FIRAT et al., Eur. J. Immunol., 29, 3112, 1999) ($3 \times 10^5$ cells/ml), which are deficient in TAP transporters, are incubated at 37° C. for 16 hours with various concentrations (100 µM, 10 µM, 1 µM, 0.1 µM) of each test peptide in serum-free RPMI 1640 medium supplemented with 100 ng/ml of human β2-microglobulin. Next, they are washed twice and labeled with the monoclonal antibody BB7.2 (PARHAM et al., Hum. Immunol., 3, 4, 277-299, 1981) which is specific for the HLA-A*0201 molecule, and then with a goat anti-mouse Ig antibody coupled to fluorescein isothiocyanate (FITC).

The cells are then analyzed by flow cytometry. For each concentration of peptide, the specific HLA-A*0201 fluorescence is calculated as a percentage of the fluorescence obtained with 100 µM of a reference peptide (HIVpol 589; IVGAETFYV (SEQ ID No: 1)). The relative affinity (RA) is defined as the ratio of the concentration of each peptide that induces 20% of the fluorescence obtained with 100 µM of the reference peptide, to the concentration of the reference peptide that induces 20% of the fluorescence obtained with 100 µM of said reference peptide. The lower the relative affinity, the stronger the binding of the peptide to HLA-A*0201. The mean RA for each peptide is determined from at least three independent experiments. In all the experiments, 20% of the maximum fluorescence was obtained for 1 to 3 µM of the reference peptide.

Stability:

T2 cells ($10^6$/ml) are incubated overnight at 37° C. with 100 µM of each test peptide in serum-free RPMI 1640 medium supplemented with 100 ng/ml of human β2-microglobulin. Next, they are washed four times in order to remove the free peptides, incubated with Brefeldin A (SIGMA; 10 µg/ml) for one hour in order to prevent the expression at their surface of newly synthesized HLA-A*0201 molecules, washed and incubated at 37° C. for 0, 2, 4, 6 or 8 hours. For each incubation time, the cells are then labeled, as indicated above, with the BB7.2 antibody, and analyzed by flow cytometry in order to evaluate the amount of peptide/HLA-A*0201 complex present at their surface. This amount is evaluated by means of the formula: (mean fluorescence of the T2 cells preincubated with the peptide−mean fluorescence of the T2 cells treated under similar conditions in the absence of peptide). The $DC_{50}$ (dissociation complex: DC) is defined as being the time required for the loss of 50% of the HLA-A*0201/peptide complexes stabilized at t=0.

The results of these experiments, given in table II below, show that the peptides p174, p262, p248G9 and p248D9 only have a low affinity for HLA-A*0201.

In order to increase this affinity and, consequently, their immunogenicity, the peptides p262, p248G9 and p248D9 were modified by replacing the residues located at position P2 or at the C-terminal position with anchoring residues specific for the HLA-A*0201 allele, so as to produce the variants p262L2 and p248V9. For the peptide p174, two variants were produced: in one (p174Y1), the residue at position P1 was replaced with a tyrosine, in the second (P174Y1V10), the C-terminal residue P10 was also replaced with the valine residue, liable to allow stronger anchoring.

The affinity of these variants for HLA-A*0201 was determined as described above.

The results, summarized in table II, show that the variants p262L2 and p248V9 possess a considerable binding affinity (RA=0.2 and 1.8, respectively) and form stable complexes ($DC_{50}$=6 h and 4 h, respectively). P174Y1V10 also possesses a considerable binding affinity (RA=2.5), but the stability of the complex formed appears to be insufficient.

TABLE II

| Peptides | Sequence | MAGE-A | RA | $DC_{50}$ |
|---|---|---|---|---|
| p174 | CLGLSYDGLL (SEQ ID No: 5) | 1, 2, 3, 4, 6, 12 | 41 | <2 |
| p174Y1 | YLGLSYDGLL (SEQ ID No: 12) | | 13 | <2 |
| p174Y1V10 | YLGLSYDGLV (SEQ ID No: 13) | | 2.5 | <2 |
| p248G9 | YLEYRQVPG (SEQ ID No: 6) | 2, 3, 4, 6, 10, 12 | >27 | <2 |
| p248D9 | YLEYRQVPD (SEQ ID No: 7) | 1 | 22.5 | <2 |
| p248V9 | YLEYRQVPV (SEQ ID No: 3) | | 1.8 | 4 |
| p262 | YEFLWGPRA (SEQ ID No: 8) | 1, 2, 3, 4, 6, 10, 12 | >35 | <2 |
| p262L2 | YLFLWGPRA (SEQ ID No: 14) | | 0.2 | 6 |

EXAMPLE 2

Immunogenicity of the Variant MAGE-A Peptides

Induction of Specific CTLs by Immunization with the Variant Peptides

The immunogenicity of the variant peptides p174Y1V10, p262L2 and p248V9 was evaluated by generation of CTLs on HHD transgenic mice (PASCOLO et al., J. Exp. Med., 185, 2043, 1997). These mice are β2m−/−, $D^b$−/− and express an HLA-A*0201 single chain made up of the α1 and α2 domains of HLA-A*0201 and the α3 and intracellular domains of $D^b$, linked via its N-terminal to the C-terminal of human β2-microglobulin, via a peptide of 15 amino acids.

The HHD mice are given a subcutaneous injection at the base of the tail with 100 µg of each variant peptide to be tested, emulsified in Freund's incomplete adjuvant, in the presence of 140 µg of a T-helper epitope derived from the HBV "core" antigen (128-140, sequence TPPAYRPPNAPIL).

After 11 days, spleen cells taken from the mice ($5 \times 10^7$ cells in 10 ml) are stimulated in vitro with the test peptide (10 µM). On the 6th day of culture, the populations which respond are tested in order to determine a specific cytotoxicity. The cells which respond are restimulated in vitro at one-week intervals with $2 \times 10^7$ irradiated (3000 rads) HHD spleen cells and 1 to 0.1 µM of peptide in the presence of 50 IU/ml of recombinant IL2 (Proleukin, Chiron Corp).

Cytotoxicity assays are carried out 6 days after the final stimulation.

RMAS-HHD cells are used as targets to study the cytotoxicity. The cells are obtained by transfection of murine RMAS cells with the HHD construct as described by PASCOLO et al. (J. Exp. Med., 185, 2043, 1997).

These target cells are labeled with 100 µCi of $^{51}$Cr for 90 minutes, and then washed three times and plated out in round-bottomed 96-well plates ($3\times10^3$ cells/well in 100 µl of RPMI 1640+3% of fetal calf serum). They are loaded with various concentrations of test peptide (variant, native peptide, or irrelevant control peptide), at 37° C. for 90 minutes.

Next, 100 µl of the effector cells (effector cell/target cell ratio=40/1) are added to the wells and the plates are incubated at 37° C. for 4 hours. After incubation, 100 µl of supernatant are collected and the radioactivity is measured in a γ-counter.

The percentage of specific lysis is calculated by means of the formula: [(experimental $^{51}$Cr release–spontaneous $^{51}$Cr release)/(maximum $^{51}$Cr release–spontaneous $^{51}$Cr release)]×100. In all the experiments, the spontaneous release is less than 20% of the maximum release induced with 3N HCl.

The results of these experiments are given in FIGS. 1A, 1B, and 1C.

The peptide p174Y1V10 is not capable of generating a CTL response, which was predictable given the poor stability of its complex with HLA-A*0201.

The peptide p262L2 induces CTLs capable of recognizing this peptide, but not the native p262 peptide.

On the other hand, the peptide p248V9 induces a CTL response directed not only against this variant but also against the two native peptides p248G9 and p248D9.

These results show that the variant p248V9 generates CTLs which kill the RMAS-HHD targets loaded with the variant peptide, or with the corresponding native peptide.

In the case of the peptide p262L2, the non-conservation of the antigenicity of the native peptide may be explained by the very considerable structural modification resulting from the substitution at position P2 of a glutamate residue with a leucine residue, which have very different sizes and charges.

4 days after transfection, the COS-7 cells are brought into contact with the CTL248 cells in a proportion of $5\times10^4$ CTLs per $3\times10^4$ COS-7 cells in RPMI 1640 in the presence of 10% SVF.

After incubation for 6 hours, the supernatant is removed and brought into contact with WEHI164 clone 13 mouse fibrosarcoma cells ($3\times10^4$ per well), which are characterized by a high sensitivity to TNF-α-induced apoptosis. In order to quantify the amount of TNF in the culture supernatants, a standard range of TNF-α (concentrations of 0 to $10^4$ pg/ml) is used in parallel. After incubation for 16 hours at 37° C., the viability of the WEHI-164 clone 13 cells is determined by means of an MTT colorimetric assay (SIGMA) (ESPEVIK and NISSEN MEYER, J. Immunol. Methods, 95, 99, 1986).

Figure 2:
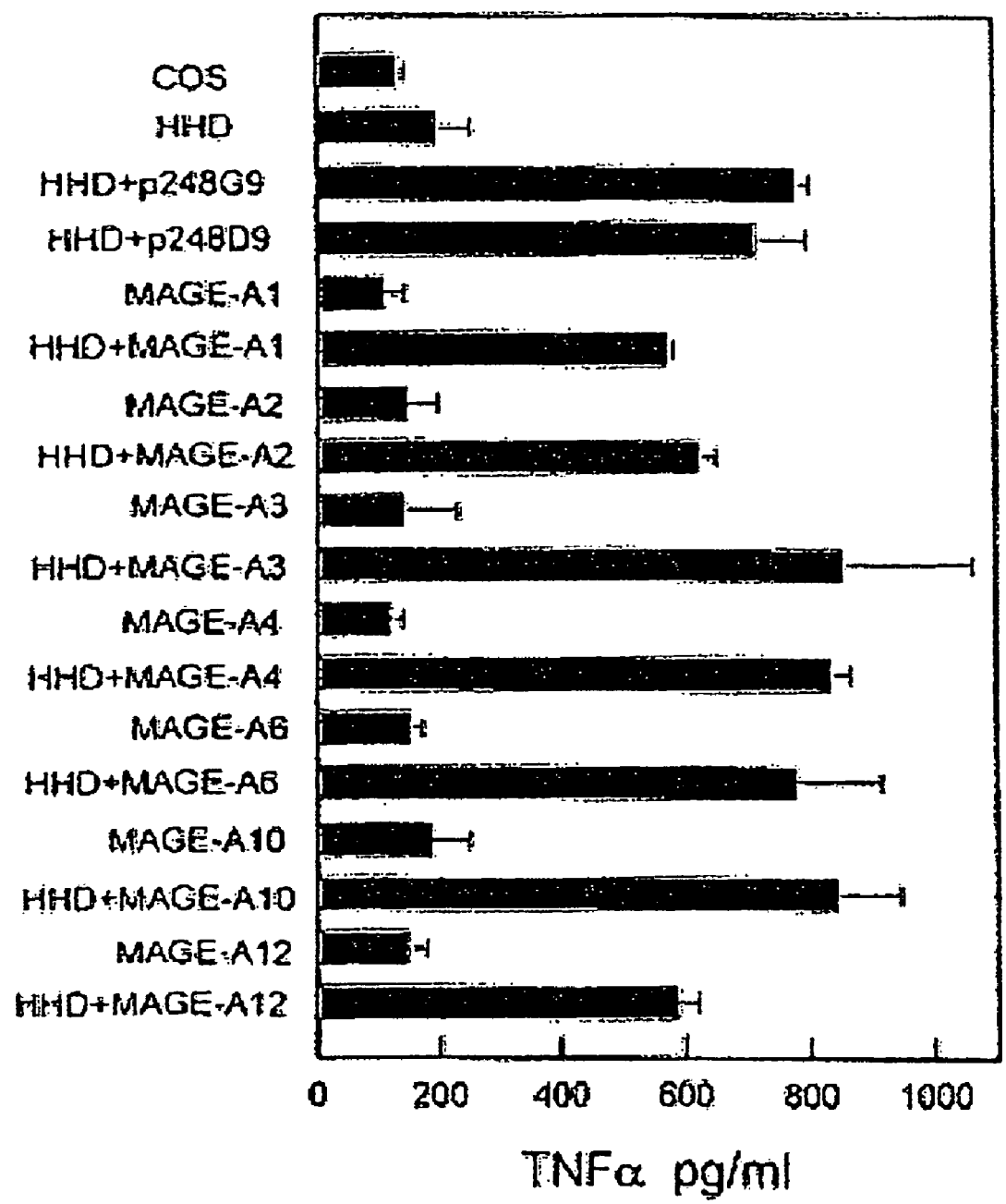
FIG. 2: Recognition of the naturally processed epitopes of MAGE-A (A1-A12) antigens by CTLs induced with the peptide p248V9, by stimulation of CTL248 cells with transfected COS-7 cells expressing MAGE-A antigens. The cells of the CTL248 line are stimulated, for each of the MAGE-A1, -A2, -A3, -A4, -A6, -A10 and -A12 antigens, with monkey COS-7 cells co-transfected with the HHD construct and a plasmid containing the cDNA for said antigen. By way of negative controls, COS-7 cells transfected either with the HHD construct alone or with the cDNA for the MAGE-A (i.e., A1-A12) antigen are used. The stimulation of the CTLs is evaluated by measuring the secretion of TNF-α. By way of a positive control, COS-7 cells transfected with the HHD construct and loaded with the peptides p248D9 and p248G9 are used. An CTL line called CTL248 was established from the spleen cells of an HHD mouse immunized with the peptide p248V9

The results are given in FIG. 2.

These results show that the CTL248 line responds to stimulation with the COS cells coexpressing HHD and a MAGE-A antigen. All the MAGE-A1, -A2, -A3, -A4, -A6, -A10 and -A12 antigens are recognized by this line.

On the other hand, no response is observed to the COS cells transfected separately with the HHD construct or with the cDNA for a MAGE-A antigen.

2) Stimulation with HLA-A*0201 Human Tumor Cells Expressing MAGE-A Antigens

The following HLA-A*0201 tumor lines were used:

lines expressing at least one MAGE-A antigen: M44 and M113 (melanoma); OBR (bladder cancer);

lines not expressing MAGE-A antigens: MCF-7 (breast cancer) and Caco-2 (colon cancer).

The HLA-A*0201 and MAGE-A expression profile for these lines is summarized in table III below.

TABLE III

| Cell line | HLA-A*0201 | MAGE-A1 | MAGE-A2 | MAGE-A3 | MAGE-A4 | MAGE-A6 | MAGE-A10 | MAGE-A12 |
|---|---|---|---|---|---|---|---|---|
| M44 | + | + | + | + | + | – | – | – |
| M113 | + | – | + | + | – | – | – | – |
| OBR | + | – | – | – | – | + | + | – |
| Caco-2 | + | – | – | – | – | – | – | – |
| MCF-7 | + | – | – | – | – | – | – | – |

Recognition of the Naturally Processed Epitopes of MAGE-A Antigens by CTLs Induced with the Peptide p248V9

A CTL line called CTL248 was established from the spleen cells of an HDD mouse immunized with the peptide p248V9, by repeated stimulation in vitro with decreasing concentrations of p248G9 (10 µM-1 µM). This line is maintained in culture in the presence of 1 µM of the peptide p248G9.

In order to test whether the cells of the CTL248 line could recognize naturally processed MAGE-A antigens, two types of experiments were carried out.

1) Stimulation with Transfected COS-7 Cells Expressing MAGE-A Antigens

The cells of the CTL248 line are stimulated, for each of the MAGE-A1, -A2, -A3, -A4, -A6, -A10 and -A12 antigens, with monkey cos-7 cells cotransfected with the HAD construct (PASCOLO et al., mentioned above) and a plasmid containing the cDNA for said antigen. By way of negative controls, COS-7 cells transfected either with the HHD construct alone or with the cDNA for the MAGE-A antigen concerned are used. The stimulation of the CTLs is evaluated by measuring their secretion of TNF-α. By way of a positive control, COS-7 cells transfected with the HHD construct and loaded with the peptides p248D9 and p248G9 are used.

The CTL248 line was stimulated with each of the tumor lines mentioned above.

The stimulation is evaluated by detecting the secretion of TNF-α as described above.

Figure 3:
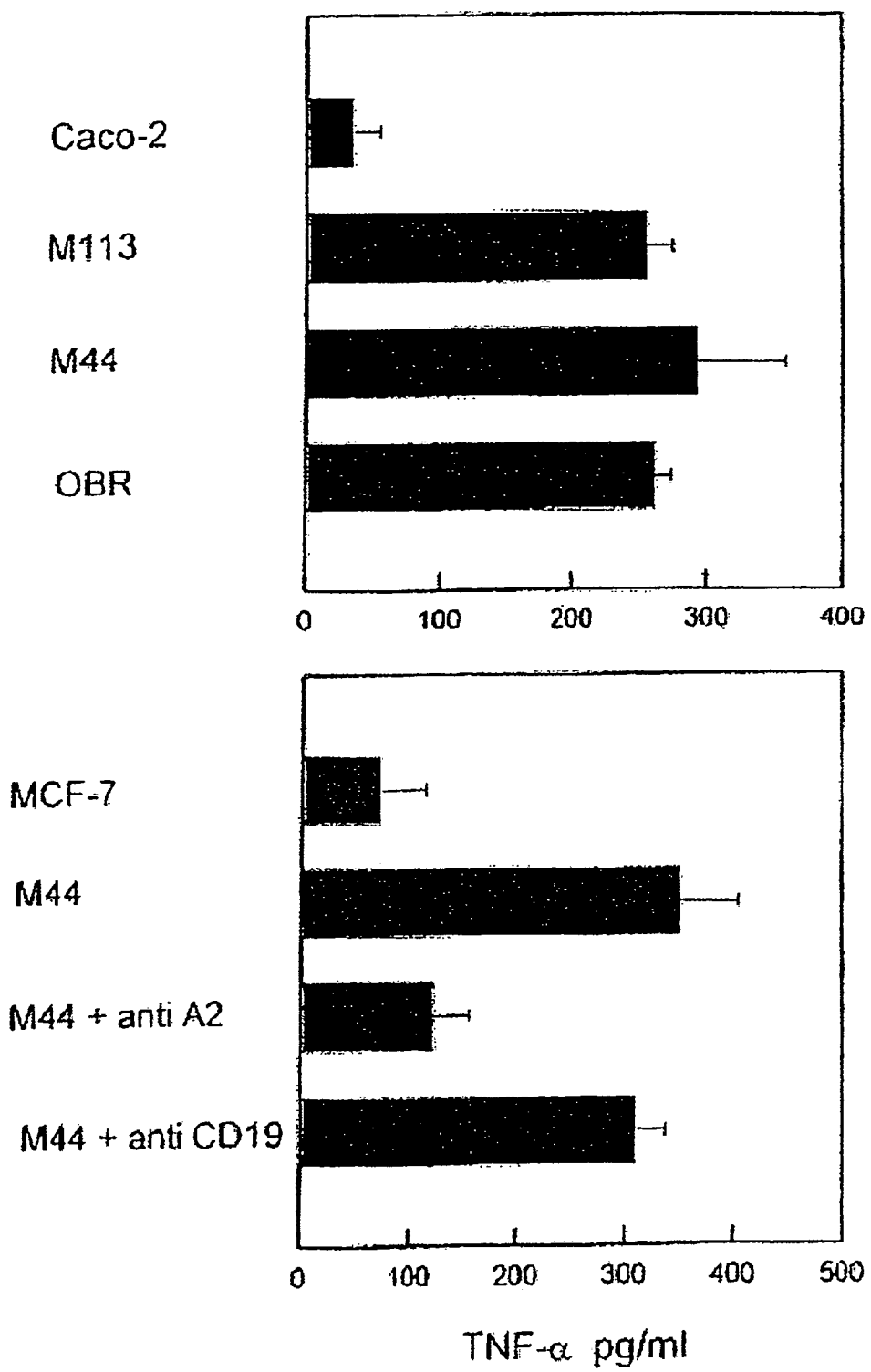
FIG. 3: Recognition of the naturally processed epitopes of MAGE-A antigens by CTLs induced with the peptide p248V9, by stimulation of CTL248 cells with HLA-A*0201 human tumor cells expressing MAGE-A antigens. The HLA-A*0201 tumor lines used in the experiment: lines expressing at least one MAGE-A antigen—M44 and M113 (melanoma); OBR (bladder cancer); and lines not expressing MAGE-A antigens—MCF-7 (breast cancer) and Caco-2 (colon cancer). Anti-CD 19 Ab is an irrelevant antibody.

The results are given in FIG. 3A, which shows that the CTL248 cells respond to stimulation with the MAGE-A+ cells, whatever the MAGE-A antigen expressed, but do not respond to the MCF-7 or Caco-2 cells which do not express MAGE-A antigen.

In order to confirm that the tumor cell recognition is indeed HLA-A*0201-restricted, the CTL248 cells were stimulated with M44 cells preincubated for one hour with an anti-HLA-A*0201 monoclonal antibody (BB7.2) or with an irrelevant antibody (anti-CD19), and the production of TNFα was measured as described above.

The results given in FIG. 3B show that only the BB7.2 antibody, which blocks HLA-A*0201, inhibits the response of the CTL248 cells.

The results of experiments 1 and 2 above show that the CTLs induced with p248V9 recognize a naturally processed epitope common to the MAGE-A1, -A2, -A3, -A4, -A6, -A10 and -A12 antigens.

Induction of Specific Human CTLs with the Peptide p248V9

The ability of p248V9 to induce CTLs in vitro using peripheral blood mononuclear cells (PBMCs) from normal donors was tested as follows.

The PBMCs are obtained, from blood samples taken by leukocytapheresis on normal donors, after centrifugation at 2000 rpm for 20 min on a Ficoll/Hypaque (Amersham) gradient. After 3 washes in 0.9% NaCl, they are resuspended in complete medium (RPMI 1640 supplemented with 10% of heat-inactivated human AB serum, 40 µg/ml of gentamicin (Panpharma) and 2 µM of L-glutamine (Gibco)), and incubated at 37° C. for 2 hours. After incubation, the non-adherent cells are removed. The adherent cells are differentiated into dendritic cells by culturing in a Teflon bag in a proportion of $3 \times 10^6$ cells/ml in complete medium supplemented with 500 IU/ml of GM-CSF (R & D Systems) and 500 IU/ml of IL-4 (R & D Systems). On the seventh day, maturing agents (100 ng/ml of polyI:C and 2 µg/ml of anti-CD40 antibody) are added to the culture. After 24 hours, the mature dendritic cells are loaded with the peptide p248V9 by incubation for 2 hours with 10 µM of peptide in the presence of 5 µg/ml of β2-microglobulin, and then irradiated at 3500 rads; they are then washed in order to remove the free peptide. CD8+ cells are isolated from the non-adherent cells by means of microbeads coupled to an anti-CD8 antibody (Miltenyi Biotec).

$2 \times 10^5$ CD8+ cells are stimulated with $2 \times 10^4$ dendritic cells loaded with the peptide, in complete medium supplemented with 1000 IU/ml of IL-6 and 5 IU/ml of IL-12 in a final volume of 100 µl/well in a 96-well plate. From the seventh day, the cultures are stimulated in vitro each week with the dendritic cells loaded with the peptide, in the presence of 20 IU/ml of IL-2 and 10 ng/ml of IL-7. After the third restimulation, the CD8+ cells are collected and stimulated with EBV-transformed HLA-A*0201 allogenic B cells, in a 1/2 ratio, in the presence of 10 µM of peptide, for 16 hours.

The IFNγ-producing CD8+ cells are purified using a commercial kit (IFNγ secretion assay-cell enrichment and detection kit, Miltenyi Biotech). The cells thus purified are cultured for one week in complete medium supplemented with 20 IU/ml of IL-2 and 10 ng/ml of IL-7.

The response of these CD8+ cells to T2 cells loaded with one of the peptides p248V9, p248G9 or p248D9, or with a irrelevant peptide (HIVgag76), or to HLA-A*0201+MAGE-A+ tumor cells (M44 and M113) or HLA-A*0201+MAGE-A− tumor cells (Caco-2), is evaluated by assaying the intracellular IFNγ production.

The CD8+ cells are incubated with the cells of the tumor line tested, in the presence of 20 µg/ml of Brefeldine-A (Sigma). After 6 hours, they are washed, labeled with an anti-CD8 antibody conjugated to r-phycoerythrin (Caltag Laboratories) in PBS for 25 min at 4° C., washed, and fixed with 4% paraformaldehyde. They are then permeabilized with saponin (Sigma) at 0.2% in PBS, and labeled with an anti-IFNγ monoclonal antibody conjugated to allophycocyanin (Pharmingen).

The cells are then analyzed by flow cytometry (FACSCalibur™ (Becton Dickinson) and CellQuest™ software).

Figure 4:
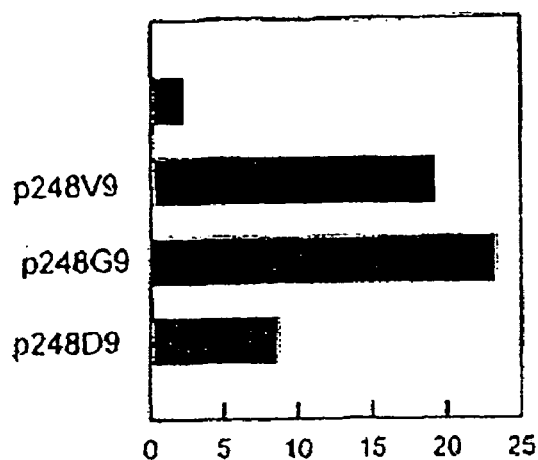
FIG. 4: Induction of specific human CTLs with the peptide p248V9. (A) shows a response of the CD8+ cells with respect to the T2 cells loaded with p248V9, p248G9 or p248D9, but not with respect to the T2 cells loaded with the irrelevant peptide. (B) shows a response of the CD8+ cells with respect to the M44 and M113 MAGE-A+ tumor lines but not with respect to the Caco-2 MAGE-A⁻ line. (C) shows, in addition, that the response with respect to the M44 line is greatly inhibited by the anti-HLA-A*0201 antibody BB7.2, but not by the irrelevant anti-CD 19 Ab antibody.
Figure 4:
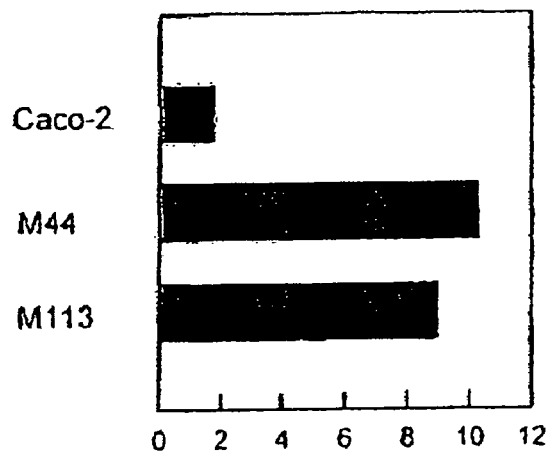
Figure 4:
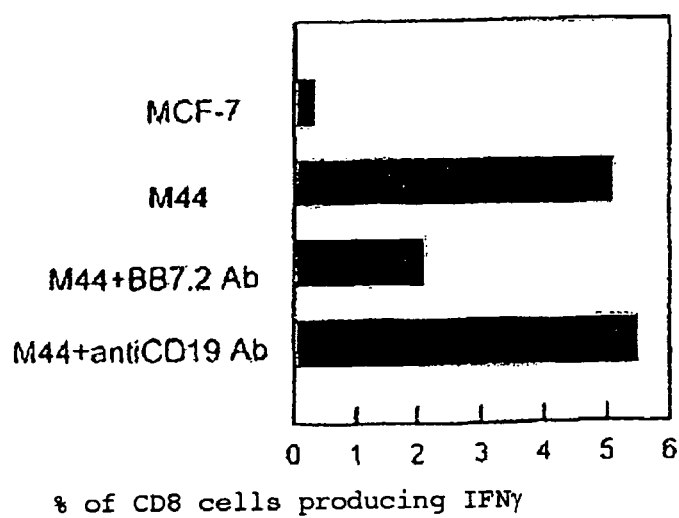

The results are given in FIG. 4: (% of cells producing IFNγ as a function of the peptide or of the tumor line tested).

FIG. 4A shows a response of the CD8+ cells with respect to the T2 cells loaded with p248V9, p248G9 or p248D9, but not with respect to the T2 cells loaded with the irrelevant peptide.

FIG. 4B shows a response of the CD8+ cells with respect to the M44 and M113 MAGE-A+ tumor lines but not with respect to the Caco-2 MAGE-A− line. FIG. 4C shows, in addition, that the response with respect to the M44 line is greatly inhibited by the anti-HLA-A*0201 antibody BB7.2, but not by the irrelevant anti-CD 19 Ab antibody.

These results demonstrate that the peptide p248V9 induces human CTLs capable of also recognizing the corresponding native peptides, and capable of recognizing tumor cells expressing varied MAGE-A antigens.

EXAMPLE 3

Identification of Epitopes Presented by the HLA-B*0702 Molecule that are Shared by the MAGE-A1, -A2, -A3, -A4, -A6, -A10 and -A12 Antigens Alignment of the MAGE-A1, -A2, -A3, -A4, -A6, -A10 and -A12 sequences reveals a group of identical 9-mers in the MAGE-A1, -A2, -A3 and -A6 sequences. The peptide derived from MAGE-A4, which has a leucine at P2, can be modified in this position by means of an L→P substitution. The peptide derived from MAGE-A12 has a phenylalanine at P3, but shares, with the peptides derived from MAGE-A1, -A2, -A3, -A4 and -A6, the sequence TKAEML (positions P4-P9). Only the peptide derived from MAGE-A10 does not contain a sequence of at least 5 amino acids common with the peptides derived from the other MAGE-A antigens.

The various groups of native peptides and the variant peptide are represented in table IV below. The residues at which the native peptides differ are indicated in bold characters.

TABLE IV

| Antigen | Native peptides | Variant peptide |
|---|---|---|
| MAGE-A1 | EPVTKAEML (SEQ ID No: 37) | EPVTKAEML (SEQ ID No: 37) |
| MAGE-A2 | EPVTKAEML (SEQ ID No: 37) | |
| MAGE-A3 | EPVTKAEML (SEQ ID No: 37) | |
| MAGE-A4 | ELVTKAEML (SEQ ID No: 39) | |
| MAGE-A6 | EPVTKAEML (SEQ ID No: 37) | |
| MAGE-A10 | EPITKAEIL (SEQ ID No: 40) | |
| MAGE-A12 | EPFTKAEML (SEQ ID No: 41) | |

EXAMPLE 4

Identification of Epitopes Presented by the HLA-A*0201 Molecule that are Shared by the HER1, HER2, HER3 and HER4 Antigens I: Identification of Candidate Peptides and Construction of Variants that are Potentially More Immunogenic:

The alignment of the sequences of the four HER proteins was carried out as described in example 1 and reveals 6 groups of 9-mers and/or of 10-mers which exhibit complete homology in the P3-P8/9 region. For each group, a variant was defined which had to have a high affinity for HLA-A*0201 and had to be capable of stimulating a cytotoxic response specific for the native peptides. The modifications involve the anchoring positions P2 and P9/10 (substitution of the amino acid of origin other than L/V/M/I with an L at P2 and with a V at P9/10) and the position P1 (substitution of the amino acid with a Y).

The various groups of native peptides and the variant peptides are represented in table V below. The residues at which the native peptides differ are indicated in bold characters.

TABLE V

| Antigen | Position of the group of peptides | Native peptides | Variant peptides |
|---|---|---|---|
| HER2 | 722 | KVKVLGSGA (SEQ ID No: 15) | YVKVLGSGV (SEQ ID No: 19) |
| HER3 | | KLKVLGSGV (SEQ ID No: 16) | |
| HER4 | | RVKVLGSGA (SEQ ID No: 17) | |
| HER1 | | KIKVLGSGA (SEQ ID No: 18) | |
| HER2 | 845 | DLAARNVLV (SEQ ID No: 20) | YLAARNVLV (SEQ ID No: 22) |
| HER3 | | NLAARNVLL (SEQ ID No: 21) | |
| HER4 | | DLAARNVLV (SEQ ID No: 20) | |
| HER1 | | DLAARNVLV (SEQ ID No: 20) | |
| HER2 | 904 | DVWSYGVTV (SEQ ID No: 23) | YVWSYGVTV (SEQ ID No: 25) |
| HER3 | | DVWSYGVTV (SEQ ID No: 23) | |
| HER4 | | DVWSYGVTI (SEQ ID No: 24) | |
| HER1 | | DVWSYGVTV (SEQ ID No: 23) | |
| HER2 | 911 | TVWELMTFGA (SEQ ID No: 26) | YVWELMTFGV (SEQ ID No: 4) |
| HER3 | | TVWELMTFGA (SEQ ID No: 26) | |
| HER4 | | TIWELMTFGG (SEQ ID No: 27) | |
| HER1 | | TVWELMTFGS (SEQ ID No: 28) | |
| HER2 | 933 | DLLEKGERL (SEQ ID No: 29) | YLLEKGERL (SEQ ID No: 31) |
| HER3 | | DLLEKGERL (SEQ ID No: 29) | |
| HER4 | | DLLEKGERL (SEQ ID No: 29) | |
| HER1 | | SILEKGERL (SEQ ID No: 30) | |
| HER2 | 945 | PICTIDVYMI (SEQ ID No: 32) | YICTIDVYMV (SEQ ID No: 36) |
| HER3 | | QICTIDVYMV (SEQ ID No: 33) | |
| HER4 | | PICTIDVYMV (SEQ ID No: 34) | |
| HER1 | | PICTIDVYKI (SEQ ID No: 35) | |

II: Affinity for HLA-A*0201 of the Selected Peptides:

The relative affinity (RA) of the selected variant peptides for HLA-A*0201 was measured as described in example 1.

The results are summarized in table VI and show that only the variant p911Y1V9 exhibits a considerable binding affinity (RA 2.03), compatible with an immunogenic nature.

TABLE VI

| Peptide | Sequence | | RA |
|---|---|---|---|
| p722Y1V9 | YVKVLGSGV | (SEQ ID No: 19) | >100 |
| p845Y | YLAARNVLV | (SEQ ID No: 22) | >100 |
| p904Y | YVWSYGVTV | (SEQ ID No: 25) | >100 |
| p911Y1V9 | YVWELMTFGV | (SEQ ID No: 4) | 2.03 |
| p933Y | YLLEKGERL | (SEQ ID No: 31) | >100 |
| p945Y1V9 | YICTIDVYMV | (SEQ ID No: 36) | >100 |

EXAMPLE 4

Immunogenicity of the Variant HER Peptides

I: Induction of Specific CTLs by Immunization with the Variant Peptides

Two CTL lines, called 1R5 and 2R5, were established from the spleen cells of HHD mice immunized with the variant peptide p911Y1V9, according to the same protocol as that described in example 1.

Cytotoxicity Assays:

Cytotoxicity assays were carried out as described in example 2. For this, RMAS-HHD target cells loaded with 10 μM of the test peptides (variant or native peptides) were incubated in the presence of cells of the two CTL lines 1R5 and 2R5.

Figure 5:
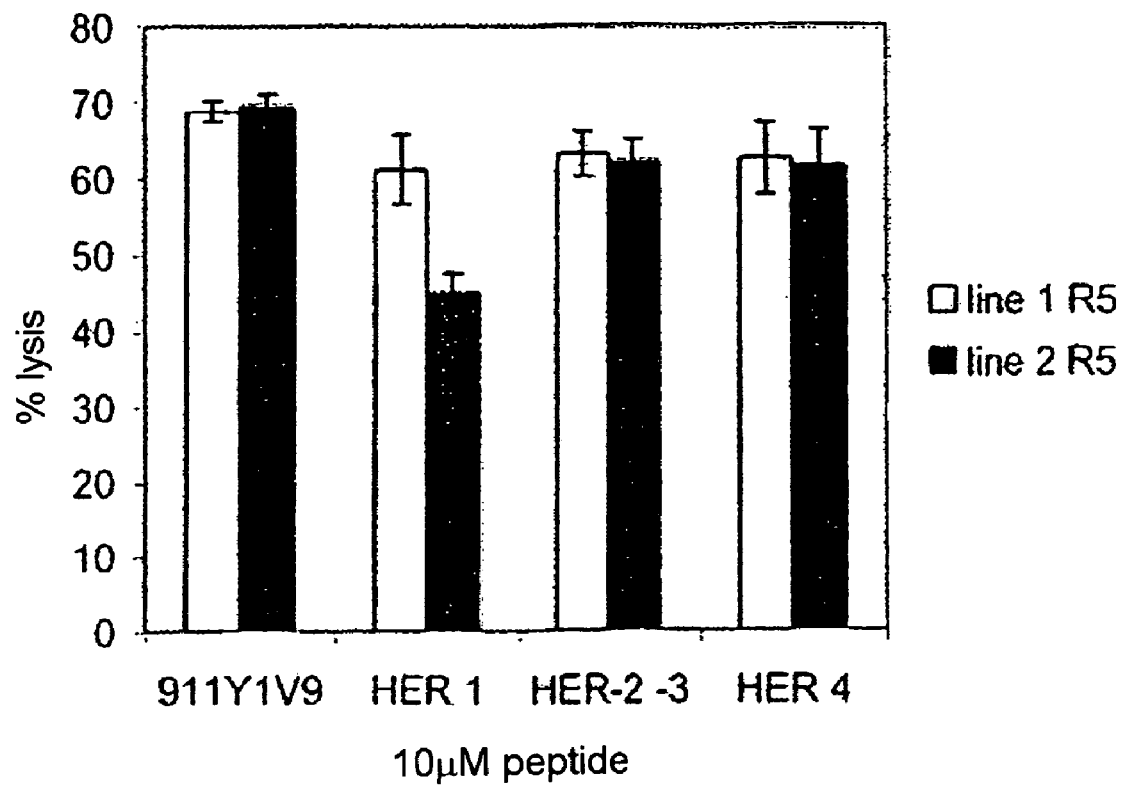
FIG. 5: Immunogenicity of the variant HER peptides, observed by cytotoxicity assays. Two CTL lines, 1R5 and 2R5, were established from the spleen cells of HHD mice immunized with the variant peptide p911Y1V9. Cytotoxicity assays: RMAS-HHD target cells loaded with 10 µM of the test peptides (variant or native peptides) were incubated in the presence of cells of the two CTL lines 1R5 and 2R5. The percentage specific lysis values observed in the presence of the 1R5 (□) and 2R5 (■) lines and for the various peptides tested are given. The cells loaded with the peptide p911Y1V9, and also the native peptides HER1 911, HER2,3 911 or HER4 911, induce a CTL response.

The percentage specific lysis values observed in the presence of the 1R5 (□) and 2R5 (■) lines and for the various peptides tested are given in FIG. 5.

The cells loaded with the peptide p911Y1V9, and also the native peptides HER1 911, HER2,3 911 or HER4 911, induce a CTL response.

These results therefore show that the variant p911Y1V9 generates CTLs which kill the RMAS-HHD target cells loaded with the variant peptide p911Y1V9, but also with the native peptides HER1 911, HER2,3 911 or HER4 911.

Intracellular IFNγ Production:

The response of the cells of the CTL line 1R5 with respect to the RMAS-HHD cells loaded with the various peptides was also evaluated by assaying the intracellular IFNγ production.

For this, the cells of the CTL line 1R5 are incubated in the presence of RMAS-HHD cells loaded with the variant peptide p911Y1V9, the native peptides HER1 911, HER2,3 911 or HER4 911, or an irrelevant peptide, and in the presence of 20 μg/ml of Brefeldine-A (Sigma). After 6 hours, the cells are washed, labeled with an anti-CD8 antibody conjugated to r-phycoerythrin, and incubated in PBS for 25 min at 4° C. They are then again washed, before being fixed with a 4% paraformaldehyde solution. The cells are then permeabilized with saponin (Sigma) at 0.2% in PBS, and labeled with an anti-IFNγ monoclonal antibody conjugated to allophycocyanin (Pharmingen).

The cells are then analyzed by flow cytometry (FACSCalibur™ (Becton Dickinson) and CellQuest™ software).

Figure 6:
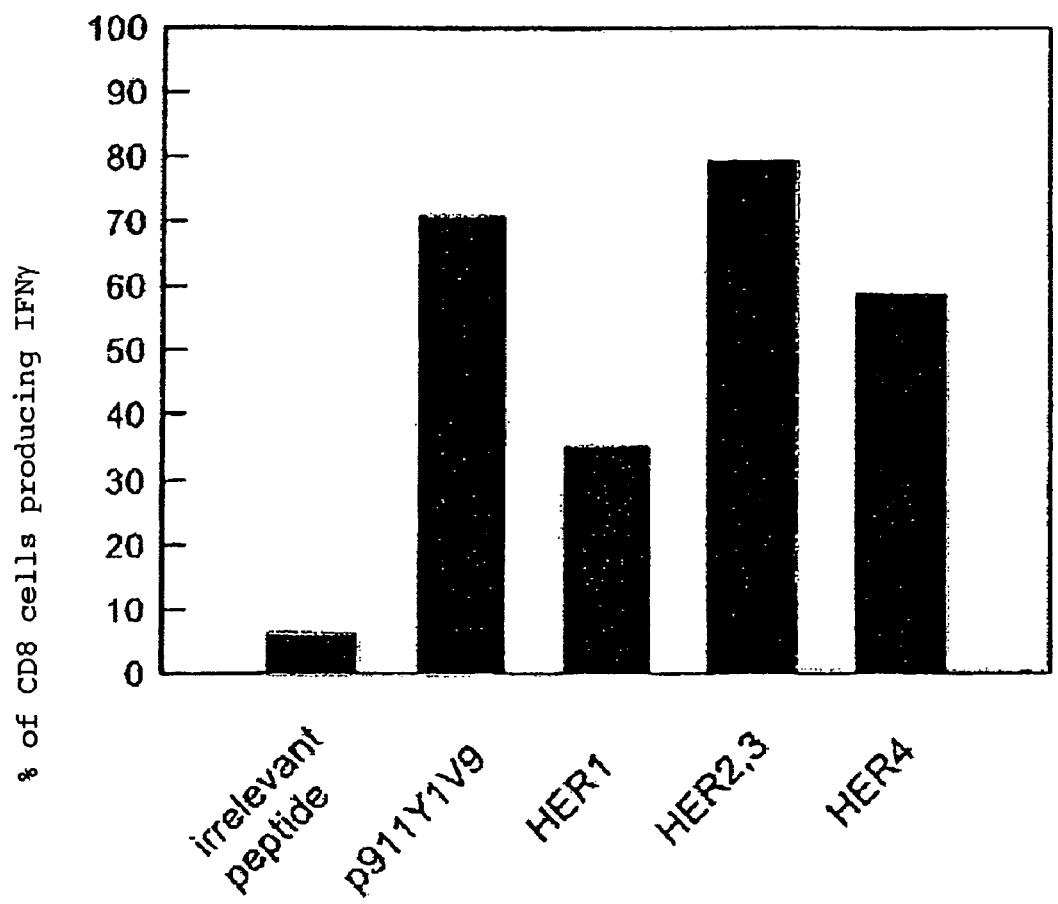
FIG. 6: Immunogenicity of the variant HER peptides, observed by intracellular IFNγ production. A response of the CD8+ cells of the CTL line 1R5 with respect to the RMAS-HHD cells loaded with the variant peptide p911Y1V9, or with the native peptides HER1 911, HER2,3 911 or HER4 911, but not with respect to the RMAS-HHD cells loaded with the irrelevant peptide, is shown.

The results are given in FIG. 6: (% of cells producing IFNγ in the presence of the RMAS-HHD cells loaded with the various test peptides).

FIG. 6 shows, as described in FIG. 5, a response of the CD8+ cells of the CTL line 1R5 with respect to the RMAS-HHD cells loaded with the variant peptide p911Y1V9, or with the native peptides HER1 911, HER2,3 911 or HER4 911, but not with respect to the RMAS-HHD cells loaded with the irrelevant peptide.

These results confirm that the peptide p911Y1V9 induces CTLs capable of recognizing this variant peptide, but also the native peptides from which it is derived.

The invention claimed is:

1. An isolated immunogenic peptide consisting of the amino acid sequence SEQ ID NO: 3.

2. A composition comprising the isolated immunogenic peptide of claim 1.

3. A medicinal product comprising the isolated immunogenic peptide of claim 1.

* * * * *

SEQUENCE LISTING

<160> NUMBER OF SEQ ID NOS: 41

<210> SEQ ID NO 1
<211> LENGTH: 9
<212> TYPE: PRT
<213> ORGANISM: Homo sapiens

<400> SEQUENCE: 1

Ile Val Gly Ala Glu Thr Phe Tyr Val
1               5

<210> SEQ ID NO 2
<211> LENGTH: 10
<212> TYPE: PRT
<213> ORGANISM: Homo sapiens

<400> SEQUENCE: 2

Arg Pro His Glu Arg Asn Gly Phe Thr Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: modified peptide

<400> SEQUENCE: 3

Tyr Leu Glu Tyr Arg Gln Val Pro Val
1               5

<210> SEQ ID NO 4
<211> LENGTH: 10
<212> TYPE: PRT
<213> ORGANISM: Artificial Sequence
<220> FEATURE:
<223> OTHER INFORMATION: modified peptide

<400> SEQUENCE: 4

Tyr Val Trp Glu Leu Met Thr Phe Gly Val
1               5                   10

<210> SEQ ID NO 5
<211> LENGTH: 10
<212> TYPE: PRT
<213> ORGANISM: Homo sapiens

<400> SEQUENCE: 5

Cys Leu Gly Leu Ser Tyr Asp Gly Leu Leu
1               5                   10

```
<210> SEQ ID NO 6
<211> LENGTH: 9
<212> TYPE: PRT
<213> ORGANISM: Homo sapiens

<400> SEQUENCE: 6

Tyr Leu Glu Tyr Arg Gln Val Pro Gly
1               5

<210> SEQ ID NO 7
<211> LENGTH: 9
<212> TYPE: PRT
<213> ORGANISM: Homo sapiens

<400> SEQUENCE: 7

Tyr Leu Glu Tyr Arg Gln Val Pro Asp
1               5

<210> SEQ ID NO 8
<211> LENGTH: 9
<212> TYPE: PRT
<213> ORGANISM: Homo sapiens

<400> SEQUENCE: 8

Tyr Glu Phe Leu Trp Gly Pro Arg Ala
1               5

<210> SEQ ID NO 9
<211> LENGTH: 9
<212> TYPE: PRT
<213> ORGANISM: Homo sapiens

<400> SEQUENCE: 9

Phe Leu Trp Gly Pro Arg Ala Leu Val
1               5

<210> SEQ ID NO 10
<211> LENGTH: 9
<212> TYPE: PRT
<213> ORGANISM: Homo sapiens

<400> SEQUENCE: 10

Phe Leu Trp Gly Pro Arg Ala Leu Ile
1               5

<210> SEQ ID NO 11
<211> LENGTH: 9
<212> TYPE: PRT
<213> ORGANISM: Homo sapiens

<400> SEQUENCE: 11

Phe Leu Trp Gly Pro Arg Ala Leu Ala
1               5

<210> SEQ ID NO 12
<211> LENGTH: 10
<212> TYPE: PRT
<213> ORGANISM: Artificial Sequence
<220> FEATURE:
<223> OTHER INFORMATION: modified peptide

<400> SEQUENCE: 12

Tyr Leu Gly Leu Ser Tyr Asp Gly Leu Leu
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: modified peptide

<400> SEQUENCE: 13

Tyr Leu Gly Leu Ser Tyr Asp Gly Leu Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: modified peptide

<400> SEQUENCE: 14

Tyr Leu Phe Leu Trp Gly Pro Arg Ala
1               5

<210> SEQ ID NO 15
<211> LENGTH: 9
<212> TYPE: PRT
<213> ORGANISM: Homo sapiens

<400> SEQUENCE: 15

Lys Val Lys Val Leu Gly Ser Gly Ala
1               5

<210> SEQ ID NO 16
<211> LENGTH: 9
<212> TYPE: PRT
<213> ORGANISM: Homo sapiens

<400> SEQUENCE: 16

Lys Leu Lys Val Leu Gly Ser Gly Val
1               5

<210> SEQ ID NO 17
<211> LENGTH: 9
<212> TYPE: PRT
<213> ORGANISM: Homo sapiens

<400> SEQUENCE: 17

Arg Val Lys Val Leu Gly Ser Gly Ala
1               5

<210> SEQ ID NO 18
<211> LENGTH: 9
<212> TYPE: PRT
<213> ORGANISM: Homo sapiens

<400> SEQUENCE: 18

Lys Ile Lys Val Leu Gly Ser Gly Ala
1               5

<210> SEQ ID NO 19
<211> LENGTH: 9
<212> TYPE: PRT
<213> ORGANISM: Artificial Sequence
<220> FEATURE:
<223> OTHER INFORMATION: modified peptide

<400> SEQUENCE: 19
```

Tyr Val Lys Val Leu Gly Ser Gly Val
1               5

<210> SEQ ID NO 20
<211> LENGTH: 9
<212> TYPE: PRT
<213> ORGANISM: Homo sapiens

<400> SEQUENCE: 20

Asp Leu Ala Ala Arg Asn Val Leu Val
1               5

<210> SEQ ID NO 21
<211> LENGTH: 9
<212> TYPE: PRT
<213> ORGANISM: Homo sapiens

<400> SEQUENCE: 21

Asn Leu Ala Ala Arg Asn Val Leu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: modified peptide

<400> SEQUENCE: 22

Tyr Leu Ala Ala Arg Asn Val Leu Val
1               5

<210> SEQ ID NO 23
<211> LENGTH: 9
<212> TYPE: PRT
<213> ORGANISM: Homo sapiens

<400> SEQUENCE: 23

Asp Val Trp Ser Tyr Gly Val Thr Val
1               5

<210> SEQ ID NO 24
<211> LENGTH: 9
<212> TYPE: PRT
<213> ORGANISM: Homo sapiens

<400> SEQUENCE: 24

Asp Val Trp Ser Tyr Gly Val Thr Ile
1               5

<210> SEQ ID NO 25
<211> LENGTH: 9
<212> TYPE: PRT
<213> ORGANISM: Artificial Sequence
<220> FEATURE:
<223> OTHER INFORMATION: modified peptide

<400> SEQUENCE: 25

Tyr Val Trp Ser Tyr Gly Val Thr Val
1               5

<210> SEQ ID NO 26
<211> LENGTH: 10
<212> TYPE: PRT
<213> ORGANISM: Homo sapiens

```
<400> SEQUENCE: 26

Thr Val Trp Glu Leu Met Thr Phe Gly Ala
1               5                   10

<210> SEQ ID NO 27
<211> LENGTH: 10
<212> TYPE: PRT
<213> ORGANISM: Homo sapiens

<400> SEQUENCE: 27

Thr Ile Trp Glu Leu Met Thr Phe Gly Gly
1               5                   10

<210> SEQ ID NO 28
<211> LENGTH: 10
<212> TYPE: PRT
<213> ORGANISM: Homo sapiens

<400> SEQUENCE: 28

Thr Val Trp Glu Leu Met Thr Phe Gly Ser
1               5                   10

<210> SEQ ID NO 29
<211> LENGTH: 9
<212> TYPE: PRT
<213> ORGANISM: Homo sapiens

<400> SEQUENCE: 29

Asp Leu Leu Glu Lys Gly Glu Arg Leu
1               5

<210> SEQ ID NO 30
<211> LENGTH: 9
<212> TYPE: PRT
<213> ORGANISM: Homo sapiens

<400> SEQUENCE: 30

Ser Ile Leu Glu Lys Gly Glu Arg Leu
1               5

<210> SEQ ID NO 31
<211> LENGTH: 9
<212> TYPE: PRT
<213> ORGANISM: Artificial Sequence
<220> FEATURE:
<223> OTHER INFORMATION: modified peptide

<400> SEQUENCE: 31

Tyr Leu Leu Glu Lys Gly Glu Arg Leu
1               5

<210> SEQ ID NO 32
<211> LENGTH: 10
<212> TYPE: PRT
<213> ORGANISM: Homo sapiens

<400> SEQUENCE: 32

Pro Ile Cys Thr Ile Asp Val Tyr Met Ile
1               5                   10

<210> SEQ ID NO 33
<211> LENGTH: 10
<212> TYPE: PRT
<213> ORGANISM: Homo sapiens
```

```
<400> SEQUENCE: 33

Gln Ile Cys Thr Ile Asp Val Tyr Met Val
1               5                   10

<210> SEQ ID NO 34
<211> LENGTH: 10
<212> TYPE: PRT
<213> ORGANISM: Homo sapiens

<400> SEQUENCE: 34

Pro Ile Cys Thr Ile Asp Val Tyr Met Val
1               5                   10

<210> SEQ ID NO 35
<211> LENGTH: 10
<212> TYPE: PRT
<213> ORGANISM: Homo sapiens

<400> SEQUENCE: 35

Pro Ile Cys Thr Ile Asp Val Tyr Lys Ile
1               5                   10

<210> SEQ ID NO 36
<211> LENGTH: 10
<212> TYPE: PRT
<213> ORGANISM: Artificial Sequence
<220> FEATURE:
<223> OTHER INFORMATION: modified peptide

<400> SEQUENCE: 36

Tyr Ile Cys Thr Ile Asp Val Tyr Met Val
1               5                   10

<210> SEQ ID NO 37
<211> LENGTH: 9
<212> TYPE: PRT
<213> ORGANISM: Homo sapiens

<400> SEQUENCE: 37

Glu Pro Val Thr Lys Ala Glu Met Leu
1               5

<210> SEQ ID NO 38
<211> LENGTH: 10
<212> TYPE: PRT
<213> ORGANISM: Homo sapiens

<400> SEQUENCE: 38

Arg Glu Pro Val Thr Lys Ala Glu Met Leu
1               5                   10

<210> SEQ ID NO 39
<211> LENGTH: 9
<212> TYPE: PRT
<213> ORGANISM: Homo sapiens

<400> SEQUENCE: 39

Glu Leu Val Thr Lys Ala Glu Met Leu
1               5

<210> SEQ ID NO 40
<211> LENGTH: 9
<212> TYPE: PRT
<213> ORGANISM: Homo sapiens
```

```
<400> SEQUENCE: 40

Glu Pro Ile Thr Lys Ala Glu Ile Leu
1               5

<210> SEQ ID NO 41
<211> LENGTH: 9
<212> TYPE: PRT
<213> ORGANISM: Homo sapiens

<400> SEQUENCE: 41

Glu Pro Phe Thr Lys Ala Glu Met Leu
1               5
```